United States Patent [19]

Gross et al.

[11] 4,268,253
[45] May 19, 1981

[54] DOWEL POST FOR DENTAL AND MEDICAL PROSTHETIC DEVICES

[76] Inventors: Michael J. Gross, 14 Edith Rd., London, England, W 14; Christopher H. Turner, Cherry Tree Cottage, Hursley, Nr. Winchester, Hampshire, England

[21] Appl. No.: 107,270

[22] Filed: Dec. 26, 1979

[51] Int. Cl.³ .............................................. A61C 5/08
[52] U.S. Cl. .................................... 433/221; 433/174
[58] Field of Search ............... 433/225, 173, 174, 175, 433/220, 221

[56] References Cited

U.S. PATENT DOCUMENTS

| 659,196 | 10/1900 | Johnson | 433/221 |
|---|---|---|---|
| 1,307,446 | 6/1919 | Kerr | 433/102 |
| 2,536,669 | 1/1951 | Thau-Jensen | 433/221 |
| 3,364,575 | 1/1968 | Baker | 433/225 |
| 3,499,222 | 3/1970 | Linkow et al. | 433/174 |
| 3,672,058 | 6/1972 | Nikoghossian | 433/174 |
| 3,928,915 | 12/1975 | Ellman | 433/225 |
| 4,103,422 | 8/1978 | Weiss et al. | 433/174 |

FOREIGN PATENT DOCUMENTS

| 2255916 | 5/1974 | Fed. Rep. of Germany | 433/174 |
|---|---|---|---|
| 1013516 | 7/1952 | France | 433/220 |
| 79399 | 1/1934 | Sweden | 433/221 |

Primary Examiner—Gene Mancene
Assistant Examiner—John J. Wilson
Attorney, Agent, or Firm—Spellman, Joel & Pelton

[57] ABSTRACT

A dowel post for securing dental and medical prostheses is provided having improved retention when cemented in a parallel-sided blind hole, and which reduces build-up of hydrostatic pressure ahead of the post as it is inserted. The dowel post comprises a head on which said prosthesis is formed or mounted and a shaft extending downwardly therefrom having a channel formed therealong providing a flow path for the cement. The channel is formed by one or more and preferably four or five helical concave flutes wound about the axis of the post at a pitch angle to the axis of 70° or less and preferably at about 45°.

6 Claims, 6 Drawing Figures

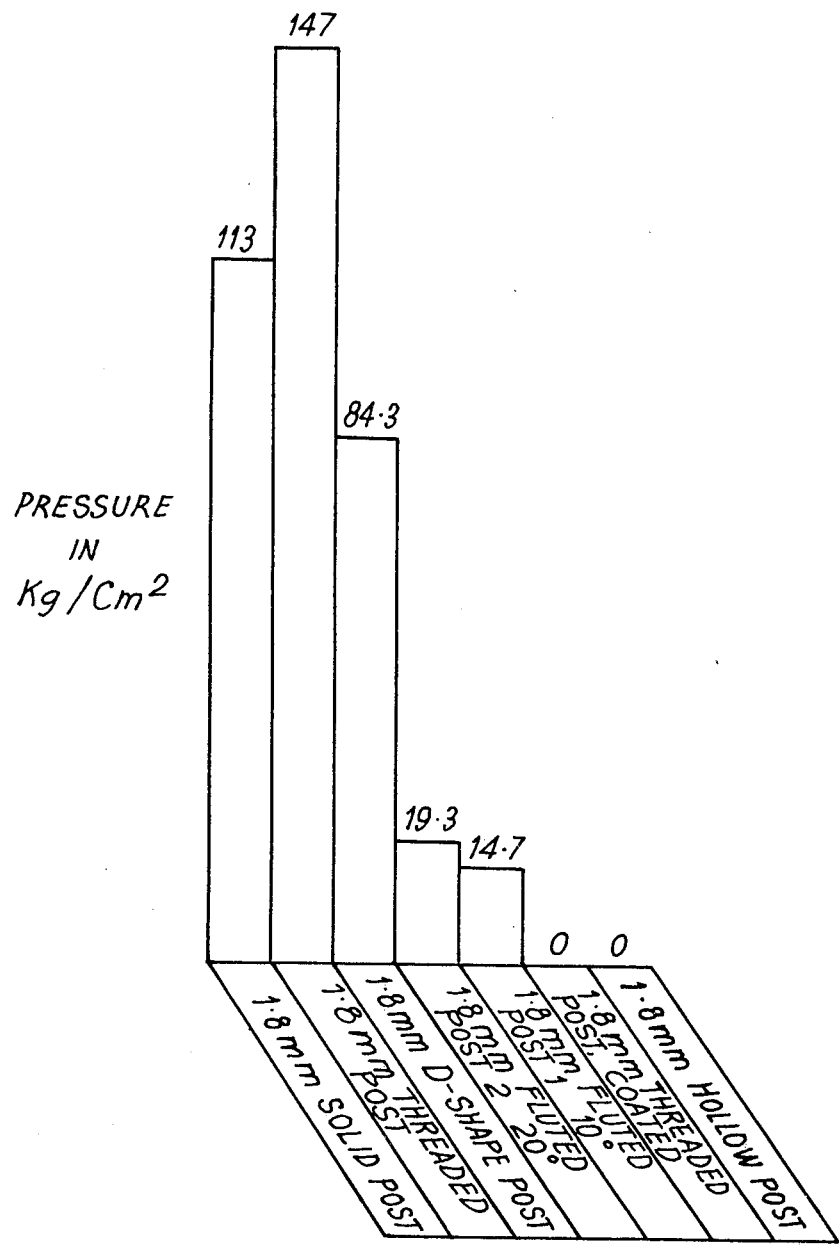

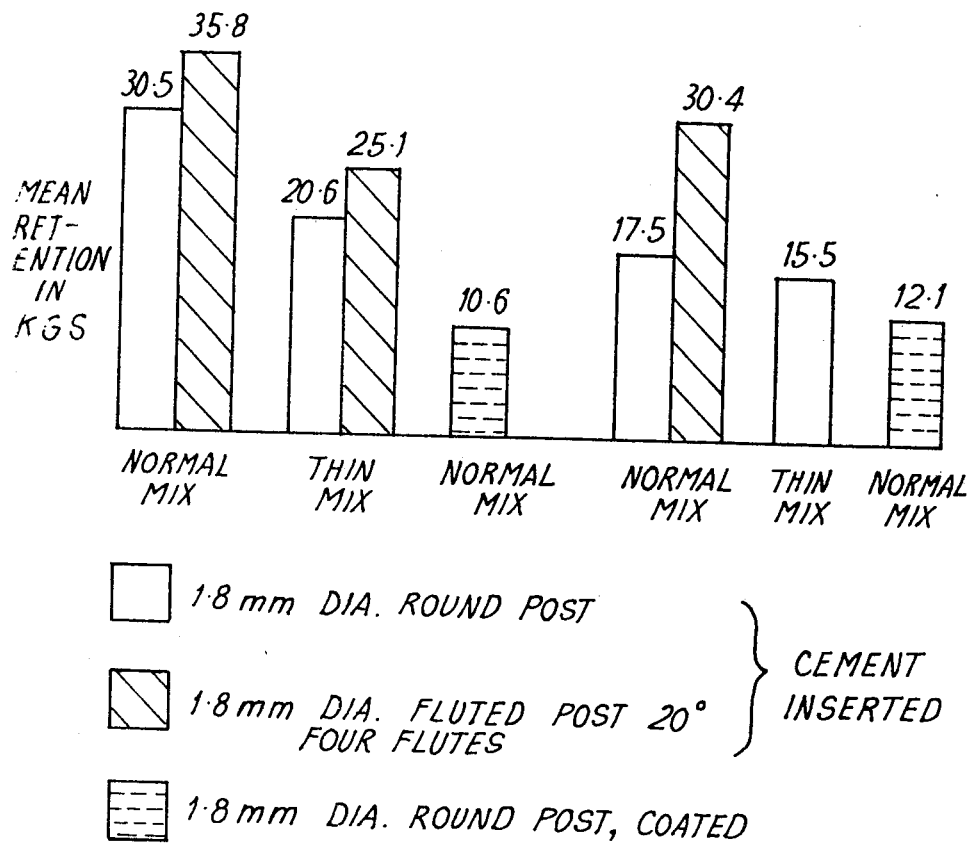

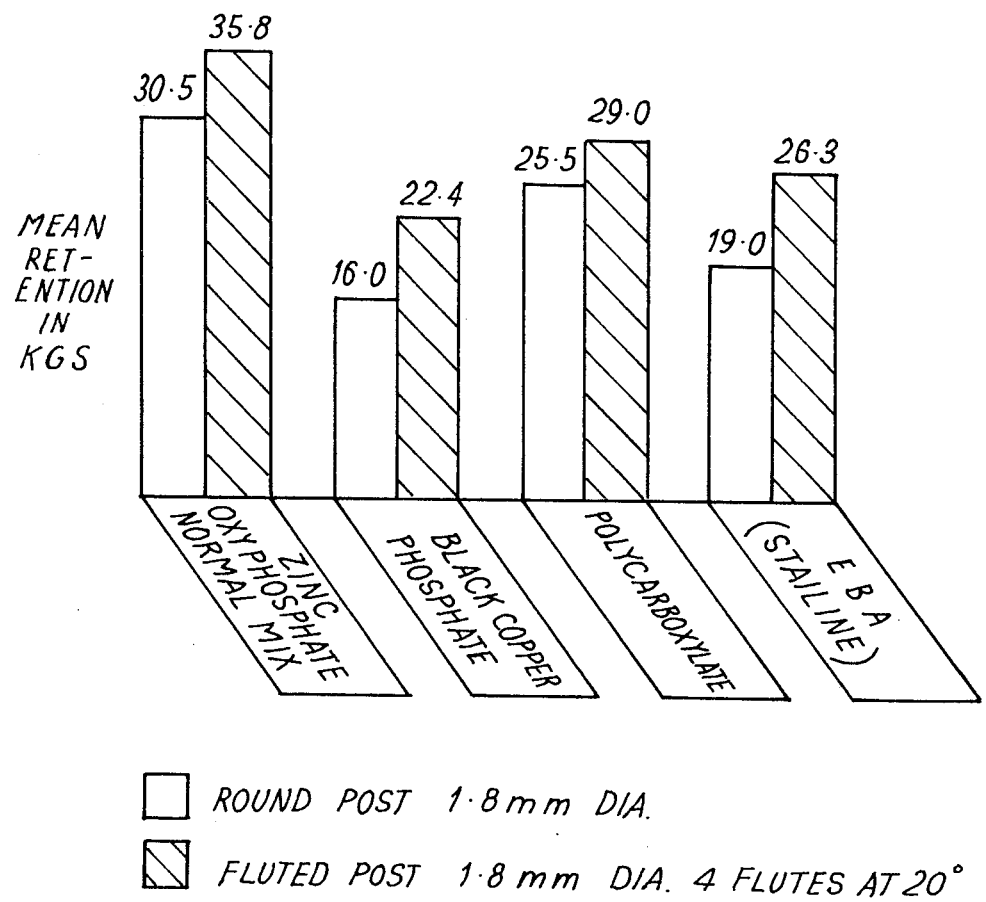

900
DOWEL POST FOR DENTAL AND MEDICAL PROSTHETIC DEVICES

BACKGROUND OF THE INVENTION

This invention relates to dental and medical prosthetic devices, more particularly a dowel post for anchoring such prosthetic devices in position.

The invention will be particularly described with reference to dowel posts for anchoring dental crowns in dental restoration work, but it will be understood that the principles of the invention can be applied in other branches of dental or medical surgery or treatment wherein an anchor is required for securing a prosthetic device in position, for example, the securing in position of an artificial joint by means of a post anchored in a bone.

In dental restoration work, post crowns are generally mounted on a dowel post which is inserted and secured in a previously prepared hole in the root of the tooth to be crowned. Various designs and configurations have been proposed for the post itself and various methods have been used to secure the dowel post in position in the tooth root. One of the simplest techniques is to use a plain parallel-sided dowel post which is inserted into a previously prepared, parallel-sided blind hole in the root and secured therein by means of a cement. Tapered posts have also been proposed, as well as posts possessing both tapered and parallel sections, although, in general, such posts show less final retention strength then parallel-sided posts. Threaded posts have also been proposed, e.g. U.K. Pat. No. 1,092,982, but these have the disadvantage of requiring a thread to be tapped in the root of the tooth, a process which is difficult to carry out owing to the poor receptivity of dentine to the cutting of the thread therein. Threaded crowns also tend to work loose unless additionally secured by a cement, which brings further problems.

Generally speaking, where a cement is used two major problems arise, namely: obtaining an adequate distribution and thickness of cement between the post and the sides of the prepared hole in the tooth root, and secondly, the avoidance of hydrostatic pressure which may build up ahead of the post as it is inserted, either by virtue of an air bubble trapped ahead of the post, or by an accumulation of cement in the bottom of the hole due to the wiping action of the post on the walls of the hole as the post is inserted. Generally, the cement is applied either by lining the hole with cement before insertion of the post, or by applying the cement to the post before insertion or a combination of the two. The former technique, whilst usually obtaining a complete or substantially complete distribution of the cement around the post is particularly prone to the build-up of hydrostatic pressure ahead of the post as it is pushed into the prepared hole, and this at best will limit the depth to which the post can be inserted, but may also result in the fracture of the tooth root. Application of the cement to the post prior to insertion substantially avoids the problem of hydrostatic pressure due to the trapping of cement ahead of the post during insertion, but almost invariably the act of inserting the post leads to the wiping off of a substantial proportion of the cement from the post, with the result that an incomplete and uneven cement distribution is obtained, which in turn, results in low retention strength. Lining the hole is therefore the preferred technique, but at the risk of hydrostatic pressure build up in the tooth root. To relieve this pressure build-up, and also air pressure which may likewise build up due to the tight fit between the post and the hole, it has been proposed (Swiss Pat. No. 424,086) to provide a channel or groove in the surface of the post and extending longitudinally thereof to provide a passageway for venting excess cement and/or air pressure from in front of the post as it is inserted into the blind hole. This, however, still does not solve the problem of obtaining uniform cement distribution and preventing wiping-off of the cement during insertion.

SUMMARY OF THE INVENTION

The present invention relates to a new and improved dowel post for dental and medical prosthetic devices. In accordance with the invention, we have developed a new post configuration, which improves the distribution of cement between the post and the hole, reduces pressure build-up ahead of the post during insertion, and generally obtains retention strengths substantially higher than that obtained with conventional parallel-sided or tapered posts, whether with the longitudinal venting groove or without.

In accordance with this invention, this is achieved by forming the shaft of the dowel post, i.e. the part which is to be received into the blind hole, with at least one concave flute formed in the surface thereof and helically wound thereabout at a pitch angle of 70° or less to the axis of the post. Optimum retention is obtained at pitch angles in the range 20°–60°, with the preferred angle being about 45°. Preferably four or five flutes are provided helically wound about the shaft along the length thereof and giving the shaft a polygonal cross-section, and an oblique section having a scalloped outline. The flutes may extend only partway along the shaft portion of the dowel post, but preferably extend along substantially the whole length thereof.

An object of this invention is to provide a new and improved dowel post for dental and medical prosthetic devices.

Another object of this invention is to provide a new and improved dowel post for dental and medical prosthetic devices wherein the shaft of the post includes at least one concave flute formed in the surface thereof.

A more specific object of this invention is to provide a new and improved medical or dental dowel post to reduce pressure build-up during insertion into a blind hole and improve retention strength wherein the shaft of the post includes a plurality of concave flutes wound helically thereabout at a predetermined pitch angle.

BRIEF DESCRIPTION OF THE DRAWINGS

The invention is further described with reference to the accompanying drawings, in which:

FIGS. 4–6 are block diagrams showing the reduction of hydrostatic pressures and the increase in retention strength obtained using posts according to the invention in dental crowns.

DETAILED DESCRIPTION OF THE INVENTION

Figure 1:
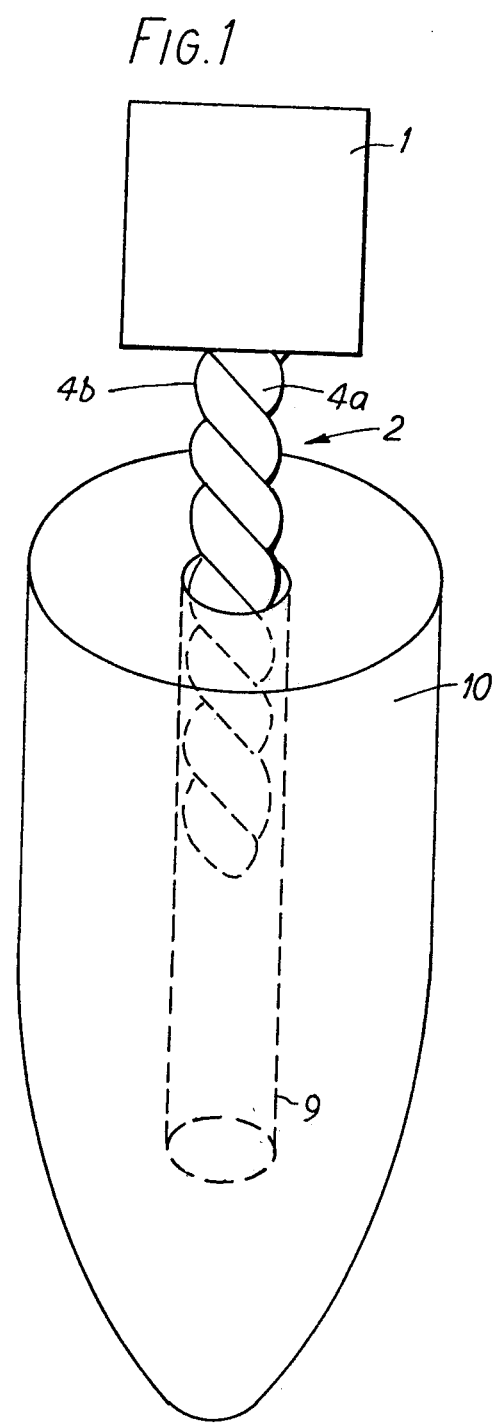
FIG. 1 is a diagrammatic view of a dowel post in accordance with the invention for use in securing a dental crown.
Figure 2:
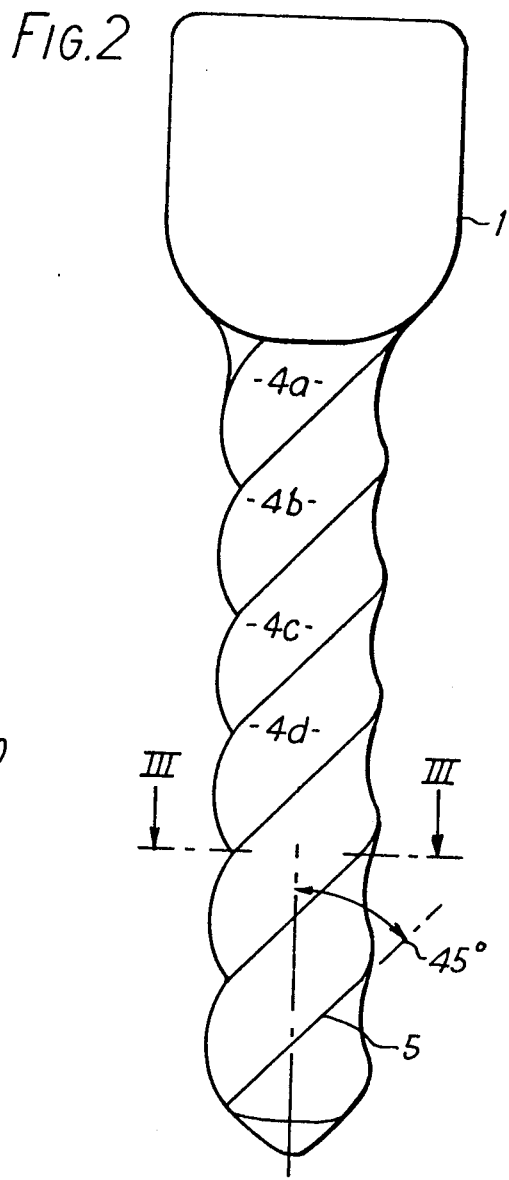
FIG. 2 is an enlarged view of the post shown in FIG. 1.

Referring to the drawings, the dowel post of this invention for securing dental crowns comprises a head 1 upon which the crown can be built up or secured in a conventional manner and a shaft 2 by means of which the post can be located in a previously prepared, parallel-sided blind hole 9 in the root 10 of the tooth to be crowned.

Figure 3:
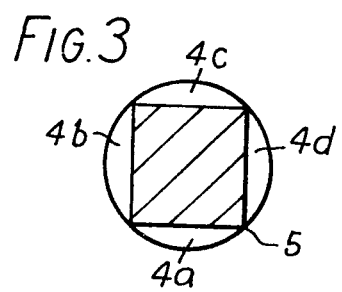
FIG. 3 is a section through the post of FIG. 2, taken on the lines III—III.

Formed in the surface of the shaft are four shallow concave flutes 4a, 4b, 4c, 4d forming four intertwined helices extending the length of the shaft 2 at an angle of 45° to the axis of the shaft. As will be seen from FIG. 3, the four helical flutes give the shaft a polygonal (square) cross-section. Also as will be seen from FIG. 3, the peaks 5 of the helical ribs formed between adjacent flutes are rounded.

The dowel post of the present invention will, of course, be manufactured from a biologically inert material, usually a metal or metal alloy, and preferably platinised gold alloy or a chrome/cobalt alloy, as are customarily used in dental and medical prostheses. Manufacture of the dowel post with the fluted shaft will generally be by investment casting, or by drawing through a polygonal die and subsequently or simultaneously twisting the drawn polygonal wire and swaging the head thereon. Other methods of suitably shaping the dowel post of the invention will be apparent to those skilled in the art.

The mounting of the dowel post of this invention in a tooth root is diagrammatically illustrated in FIG. 1. As shown, the tooth root 10 is provided in known manner with a parallel-sided blind hole 9 to the required depth. The hole is then lined with the fluting cement, which alternatively or additionally can be applied to the fluted shaft 2 of the dowel post. The shaft of the dowel post is then inserted and pressed home, possibly with a slight twisting action. Preferably, the hole diameter will correspond substantially to the maximum diameter of the shaft, i.e. the distance from the peak of the ridge formed between adjacent flutes on one side to the peak of a corresponding ridge on the opposite side of the shaft, although it is a feature of the invention that the fluted dowel posts of this invention are well retained even in oversize holes.

In the case of dowel posts for dental crowns, the dowel posts will generally have diameters ranging from 1 to 2 mm and a length of about 15 mm although longer or shorter posts may be used in certain circumstances.

Once in position, the crown, or other prosthetic device can be mounted on the head of the dowel post in conventional manner, e.g. by cementing.

The reduction of hydrostatic pressure and increased retention of dowel posts according to the invention are illustrated by the accompanying block diagrams, FIGS. 4 and 5, illustrating respectively the measured hydrostatic pressure developed inside the root of a tooth during insertion of various types of dowel post, and the retention strengths obtained using fluted posts in accordance with this invention as compared with plain parallel-sided posts. In general, tapered and grooved posts may be expected to achieve a reduction in hydrostatic pressure, although with grooved posts it has been shown that the reduction of hydrostatic pressure is only of the order of 20%, compared with 90% reduction achieved using fluted posts according to the invention, unless the groove is of relatively large dimensions in which case the retention strength is significantly reduced; but in any case, it is recognized that, in the case of grooved and tapered posts, the reduction in hydrostatic pressure is only achieved at the expense of some reduction in retention strength.

FIG. 4 shows the substantial reduction in hydrostatic pressure obtained using fluted posts according to this invention when pressed into a previously prepared, parallel-sided blind hole in an acrylic block simulating the root of a tooth, to which a pressure gauge had been fitted, the holes being lined before insertion of the post with a normal phosphate dental cement mix, as compared with a solid round section post and a post having a solid D-section, i.e. with a flat formed on one side to provide a pressure relief channel along one side thereof. The fluted posts used had a shaft length of 15 mm, a diameter of 1.8 mm and were formed with four helical flutes at a pitch angle of 10° (post 1) and 20° (post 2) to the longitudinal axis. The posts used for comparison were of similar dimensions. Also for comparison is shown the hydrostatic pressure developed on inserting a threaded post into a tapped hole lined with the same cement, although such a method is not to be recommended in practice because of the high pressure generated, and the high risk of fracture. In practice, in using a threaded post the cement is applied to the post prior to insertion, in which case the hydrostatic pressure is generally negligible.

FIG. 5 shows the increased retention strengths obtained using 1.8 mm diameter fluted posts in accordance with this invention inserted into both a close fit blind hole in an extracted tooth root and in a slightly oversize hole, using a standard zinc phosphate dental cement, as compared with values obtained using a solid round-section 1.8 mm diameter dowel post, both with the cement applied as a lining to the hole and applied to the post itself before insertion. The fluted posts had four helical flutes wound about the shaft at a pitch angle of 20°.

FIG. 6 shows the effect of different types of cement using both fluted dowel posts in accordance with this invention and as described above in connection with FIG. 5 and round section posts inserted into a previously prepared blind hole lined with the cement in question. In all cases a significant increase in retention strength is demonstrated in respect of fluted posts in accordance with this invention.

In a subsequent series of tests 1 mm diameter and 1.6 mm diameter fluted platinised gold posts in accordance with this invention, having four helical flutes at a pitch angle of 45°, were inserted as a close fit into prepared blind holes in extracted tooth roots using a normal mix zinc phosphate dental cement applied as a lining to the hole, and tested for retention strength in an Instron (Registered Trade Mark) tester. The retention strengths obtained with the 1 mm posts were in the range 36–38 kg, whilst the 1.6 mm posts gave retention strengths in the range 45–46 kg.

It is understood that the above-described arrangements are merely illustrative examples of the application. Numerous other arrangements may be readily devised by those skilled in the art which will embody the principles of the invention and fall within the spirit and scope thereof.

We claim:

1. A dowel post for anchoring a dental or medical prosthetic device comprising a head on which said device may be formed or mounted and a shaft extending therefrom for insertion into a previously prepared parallel-sided blind hole, and secured therein by a cement, wherein said shaft is of substantially constant diameter along its length and is provided with a plurality of concave flutes helically intertwined about the axis of said shaft and co-extending substantially along the length thereof at a pitch angle of 70° or less to the axis of the shaft, said concave flutes being contiguous around the circumference of the shaft, and providing said shaft with a substantially uniform polygonal section along its length.

2. A dowel post according to claim 1, wherein:
said flute(s) is or are at a pitch angle of about 45° to the axis of the shaft.

3. A dowel post according to claim 2 having four helical flutes equispaced around the shaft and coextending along the length of the shaft.

4. A dental crown comprising:
a dowel post as claimed in claim 1 and a crown member mounted on the head thereof.

5. A medical prosthetic device in the form of an artificial joint comprising:
a dowel post as claimed in claim 1 and an artificial joint member formed or mounted on the head thereof.

6. In a method of crowning a tooth root which comprises inserting a dowel post into a previously prepared, parallel-sided blind hole in the tooth root and securing the dowel post therein by means of a cement, the exposed end of the dowel post providing a point of attachment for the tooth crown, the improvement which comprises inserting into a cement-lined blind hole a dowel post having a shaft of substantially constant diameter along its length and provided on its surface with a plurality of concave flutes helically intertwined about the axis of said shaft and co-extending substantially along the length thereof at a pitch angle of 70° or less to the axis of the shaft, said concave flutes being contiguous around the circumference of the shaft, and providing said shaft with a substantially uniform polygonal section along its length.

* * * * *

UNITED STATES PATENT AND TRADEMARK OFFICE
Certificate

Patent No. 4,268,253            Patented May 19, 1981

Michael Joseph Gross and Christopher Hugh Turner

Application having been made by Michael Joseph Gross and Christopher Hugh Turner, the inventors named in the patent above identified, for the issuance of a certificate under the provisions of Title 35, Section 256, of the United States Code, deleting the name of Christopher Hugh Turner as joint inventor, and a showing and proof of facts satisfying the requirements of the said section having been submitted, it is this 24th day of Jan. 1984, certified that the name of the said Christopher Hugh Turner is hereby deleted from the said patent as joint inventor with the said Michael Joseph Gross.

Fred W. Sherling,
*Associate Solicitor.*